(12) United States Patent
Zocchi

(10) Patent No.: US 8,268,259 B2
(45) Date of Patent: *Sep. 18, 2012

(54) BLOOD GLUCOSE MONITORING KIT

(75) Inventor: Michael R. Zocchi, Somerville, MA (US)

(73) Assignee: Abbott Laboratories, Abbott Park, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 12/762,967

(22) Filed: Apr. 19, 2010

(65) Prior Publication Data

US 2010/0204558 A1 Aug. 12, 2010

Related U.S. Application Data

(63) Continuation of application No. 10/920,912, filed on Aug. 18, 2004.

(51) Int. Cl.
*B01L 3/00* (2006.01)
*A61B 5/00* (2006.01)
*B65D 85/38* (2006.01)

(52) U.S. Cl. .................. 422/430; 600/365; 206/305

(58) Field of Classification Search .................. 422/430; 600/365; 206/305
See application file for complete search history.

(56) References Cited

U.S. PATENT DOCUMENTS

| | | | |
|---|---|---|---|
| 5,015,830 A | 5/1991 | Masuzawa et al. | |
| 5,283,862 A * | 2/1994 | Lund | 345/173 |
| 5,725,090 A | 3/1998 | Vermillion et al. | |
| 5,802,940 A | 9/1998 | Jaeger | |
| 5,808,865 A * | 9/1998 | Alves | 361/679.31 |
| 6,026,961 A * | 2/2000 | McCarthy et al. | 206/576 |
| 6,071,739 A * | 6/2000 | Vadgama et al. | 435/287.9 |
| 6,149,001 A * | 11/2000 | Akins | 206/320 |
| 6,253,570 B1 * | 7/2001 | Lustig | 62/457.2 |
| 6,602,469 B1 * | 8/2003 | Maus et al. | 422/68.1 |
| 6,851,822 B2 | 2/2005 | Herrera | |
| 6,974,489 B2 * | 12/2005 | Behrens et al. | 55/385.6 |
| 7,389,872 B2 * | 6/2008 | Wheeler et al. | 206/320 |
| 2003/0021729 A1 | 1/2003 | Moller et al. | |

(Continued)

FOREIGN PATENT DOCUMENTS

DE 3409706 7/1985

(Continued)

*Primary Examiner* — Lore Jarrett
(74) *Attorney, Agent, or Firm* — Edward J. Baba; Marcus T. Hunt; Bozicevic, Field & Francis LLP

(57) ABSTRACT

A blood glucose monitoring kit includes a case constructed in the form of a bi-fold wallet which comprises an upper flap and a lower flap that are connected together through a fold. The case includes an outer layer constructed out of a water resistant and soft fabric and an inner layer constructed out of a water resistant material, the outer and inner layers being sewn together about their peripheries. A layer of cushioned material is preferably disposed between the inner and outer layers to provide the case with a soft feel. Blood glucose monitoring electronics are preferably integrated directly into the upper flap of the case, the electronics including a printed circuit board (PCB), a test port mounted on the PCB and a display mounted on the PCB. Preferably, the upper flap is provided with an opening through which the test port is externally accessible. Additionally, the upper flap is provided with a window through which the display is externally visible. A pouch is secured onto the inner surface of the lower flap and is sized and shaped to retain a plurality of disposable test components.

14 Claims, 2 Drawing Sheets

U.S. PATENT DOCUMENTS

2003/0031591 A1* 2/2003 Whitson et al. ................. 422/50
2003/0031595 A1 2/2003 Kirchhevel et al.
2003/0038047 A1 2/2003 Sleva et al.
2005/0182358 A1 8/2005 Veit et al.
2009/0054812 A1 2/2009 Mace et al.
2009/0275806 A1* 11/2009 Wu et al. ....................... 600/300

FOREIGN PATENT DOCUMENTS

DE 20006107 9/2000

* cited by examiner

BLOOD GLUCOSE MONITORING KIT

BACKGROUND OF THE INVENTION

The present invention relates generally to monitors for use in measuring the concentration of glucose in a blood sample (said monitors being commonly referred to as blood glucose monitors in the art).

There are many medical conditions which require frequent measurement of the concentration of a particular analyte in the blood of a patient. For example, diabetes is a disease which typically requires a patient to routinely measure the concentration of glucose in his/her blood. Based upon the results of each blood glucose measurement, the patient may then require a particular drug treatment (e.g., an injection of insulin) in order to regulate that the blood glucose level of the patient remains within a specified range. Exceeding the upper limit of said range (hyperglycemia) or dropping beneath the lower limit of said range (hypoglycemia) should be avoided with as much diligence as possible to prevent the patient from experiencing serious medical complications which include, inter alia, retinopathy, nephropathy, and neuropathy.

A multi-step process is commonly practiced by diabetes patients to self-monitor the level of glucose present in their blood.

In the first step of said process, a patient is required to provide a blood sample suitable for testing. Blood samples taken from a patient for blood sugar monitoring are typically obtained by piercing the skin of the patient using a lancet device. A lancet device (also commonly referred to as a lancing device) typically includes a tubular body and a removable lancet. The body is typically adapted to be held by the user, the lancet being coupled to the body and being adapted to penetrate through the epidermis (the outermost layer of the skin) of the patient and into the dermis (the layer of skin directly beneath the epidermis) which is replete with capillary beds. The puncture of one or more capillaries by the lancet generates a sample of blood which exits through the incision in the patient's skin.

In some lancet devices, the lancet extends from the body at all times. In other lancet devices, the lancet is adapted to be moved, when actuated, from a retracted position in which the lancet tip is disposed within the body to an extended position in which the lancet tip extends beyond the body. Typically, the movement of the lancet from its retracted position to its extended position is effected with such force that contact of the moving lancet tip with the skin of a patient results in the piercing of the skin of the patient. In many such lancet devices having a movable lancet, the lancet is automatically drawn back into the body after reaching its extended position (e.g., using a spring) in order to minimize the risk of inadvertent lancet sticks.

Typically, the tubular body of a lancet device is designed for multiple uses. To the contrary, each individual lancet is individually wrapped and designed for a single use. In use, the individual lancet is removed from a sealed wrapping and mounted onto the lancet body. With the lancet mounted onto the body in this manner, the lancet device can be used to acquire a blood sample. After the blood sample has been acquired, the lancet is removed from the body and is discarded. Accordingly, this type of lancet is commonly referred to as a single-use disposable lancet in the art.

In the second step of said process, a blood glucose monitoring system is utilized to measure the concentration of glucose in the blood sample. One type of glucose monitoring system which is well known and widely used in the art includes a blood glucose meter (also commonly referred to a blood glucose monitor) and a plurality of individual, disposable, electrochemical test sensors which can be removably loaded into the meter. Examples of blood glucose monitoring systems of this type are manufactured and sold by Abbott Laboratories under the PRECISION line of blood glucose monitoring systems.

Each individual electrochemical test sensor typically includes a substrate which is formed as a thin, rectangular strip of non-conductive material, such as plastic. A plurality of carbon-layer electrodes are deposited (e.g., screen printed) on the substrate along a portion of its length in a spaced apart relationship, one electrode serving as the reference electrode for the test sensor and another electrode serving as the working electrode for the test sensor. All of the conductive electrodes terminate at one end to form a reaction area for the test sensor. In the reaction area (also commonly referred to as the reactive area), an enzyme is deposited on the working electrode. When exposed to the enzyme, glucose present in a blood sample undergoes a chemical reaction which produces a measurable electrical response. The other ends of the electrical contacts are disposed to electrically contact associated conductors located in the blood glucose monitor, as will be described further below.

A blood glucose monitor is typically modular and portable in construction to facilitate its frequent handling by the patient. A blood glucose monitor often comprises a multi-function test port which is adapted to receive the test sensor in such a manner so that an electrical communication path is established therebetween. As such, an electrical reaction created by depositing a blood sample onto the reaction area of the test sensor travels along the working electrode of the test sensor and into the test port of the blood glucose monitor. Within the housing of the monitor, the test port is electrically connected to a microprocessor which controls the basic operations of the monitor. The microprocessor, in turn, is electrically connected to a memory device which is capable of storing a multiplicity of blood glucose test results.

In use, the blood glucose monitoring system of the type described above can be used in the following manner to measure the glucose level of a blood sample and, in turn, store the result of said measurement into memory as test data. Specifically, a disposable test sensor is unwrapped from its packaging and is inserted into the test port of the monitor. With the test sensor properly inserted into the monitor, there is established a direct electrical contact between the conductors on the test sensor and the conductors contained within the test port, thereby establishing an electrical communication path between the test sensor and the monitor. Having properly disposed the test sensor into the test port, the monitor typically displays a "ready" indication on its display.

The user is then required to provide a blood sample using a lancet device. Specifically, as noted above, a disposable lancet is unwrapped from its protective packaging and is loaded into a corresponding lancet device. The lancet device is then fired into the skin of the patient to provide a blood sample.

After lancing the skin, the patient is required to deposit one or more drops of blood from the patient's wound site onto the reaction area of the test sensor. When a sufficient quantity of blood is deposited on the reaction area of the test sensor, an electrochemical reaction occurs between glucose in the blood sample and the enzyme deposited on the working electrode which, in turn, produces an electrical current which decays exponentially over time. The decaying electrical current created through the chemical reaction between the enzyme and the glucose molecules in the blood sample, in turn, travels along the electrically conductive path established between the test sensor and the monitor and is measured by the microprocessor of the monitor. The microprocessor of the monitor, in turn, correlates the declining current to a standard numerical glucose value (e.g., using a scaling factor). The numerical glucose value calculated by the monitor is then shown on the monitor display for the patient to observe. In addition, the data associated with the particular blood glucose measurement is stored into the memory for the monitor.

As can be appreciated, the aforementioned method for conducting a blood glucose test necessitates the possession of a large quantity of separate components. Specifically, in order to perform a single blood glucose test using the method described above, a user is required to possess, inter alia, a reusable lancet base, a disposable lancet, a modular blood glucose monitor and a disposable test strip.

Diabetes patients often find it difficult to hold such a large quantity of individual test components. In fact, it has been found that patients often lose or misplace one or more the aforementioned components. As a result, the patient is often precluded from performing routine blood glucose tests which, in turn, can seriously jeopardize the health of the patient.

Accordingly, blood glucose monitoring kits are well known in the art. Blood glucose monitoring kits provide a patient with means for easily storing all of the components which are required to perform a test. Specifically, a blood glucose monitoring kit commonly includes an enclosable case into which all of the aforementioned components can be removably stored. As such, when a test is required, the user simply opens the case and removes the necessary components therefrom in order to perform an assay. Upon completion of the test, the reusable components are returned to the pouch and the disposable components are discarded. The pouch is then closed until such time that further testing is required.

Although useful in simplifying the handling of a large quantity of individual components, kits of the type described above suffer from a couple notable disadvantages.

As a first disadvantage, it has been found that kits of the type described above are somewhat bulky in size. In particular, the relatively large size of conventional blood glucose monitors tends to significantly increase the overall size (and, in particular, the thickness) of the kit. As a result, the patient often finds it to be considerably uncomfortable to store the kit on his/her person (e.g., in a clothing pocket) between tests, which is highly undesirable.

As a second disadvantage, the fact that all of the blood glucose testing components are removably stored within the case increases the number of preparatory steps that a patient must undertake prior to performing an assay. Specifically, the user must first open the case (e.g., by unzipping, unsnapping, etc.) in order to access the various components contained therein. With the case open, the user must then remove the lancet base and blood glucose monitor therefrom. Preferably, the monitor is then positioned on a flat and stable surface to facilitate its use. Next, the patient must remove a disposable lancet and a disposable test strip from the pouch. In turn, the disposable lancet and the disposable test strip must be unwrapped and installed into their corresponding tools. Only after completion of all these preparatory steps can the user perform an assay, which is highly undesirable.

SUMMARY OF THE INVENTION

It is an object of the present invention to provide a novel blood glucose monitoring kit.

It is another object of the present invention to provide a novel blood glucose monitoring kit which includes a case adapted to retain all of the necessary components for performing a blood glucose test.

It is yet another object of the present invention to provide a blood glucose monitoring kit as described above which is compact.

It is yet still another object of the present invention to provide a blood glucose monitoring kit as described above which has a limited number of parts, which is inexpensive to manufacture and which is easy to use.

Therefore, according to one feature of the present invention, there is provided a blood glucose monitoring kit comprising a case, said case comprising a layer of cushioned material, and blood glucose monitoring electronics at least partially integrated into said case.

Various other features and advantages will appear from the description to follow. In the description, reference is made to the accompanying drawings which form a part thereof, and in which is shown by way of illustration, various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF THE PREFERRED EMBODIMENT

Figure 1:
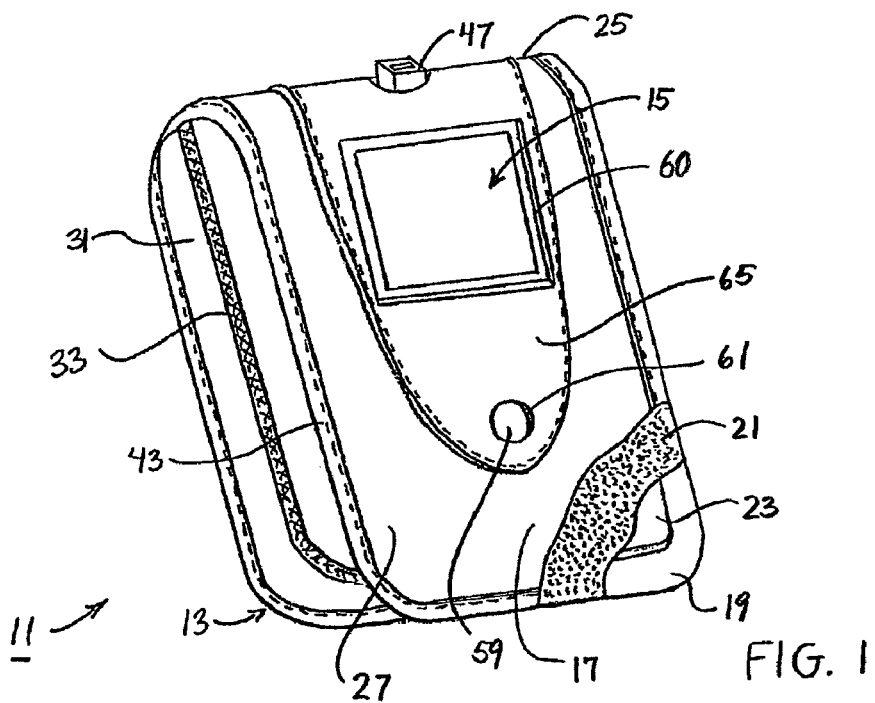
FIG. 1 is a front perspective view of a blood glucose monitoring kit constructed according to the teachings of the present invention, the kit being shown with its case closed.
Figure 2:
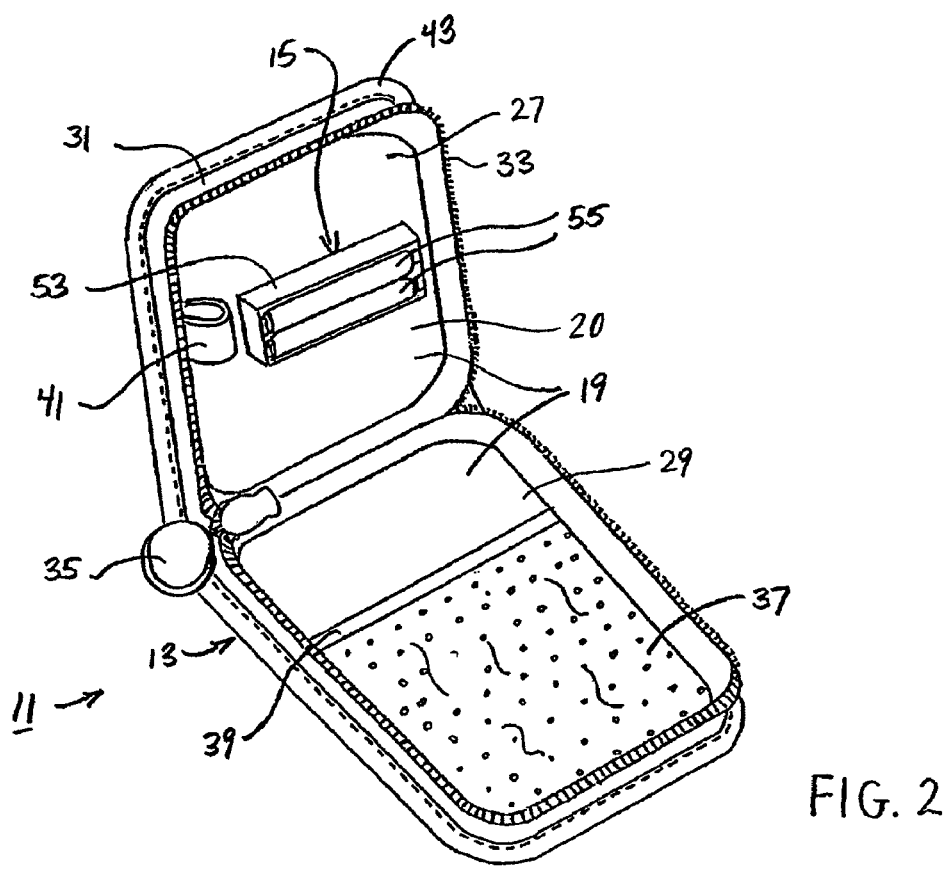
FIG. 2 is a front perspective view of the blood glucose monitoring kit shown in FIG. 1, the kit being shown with its case opened.
Figures 3, 4:
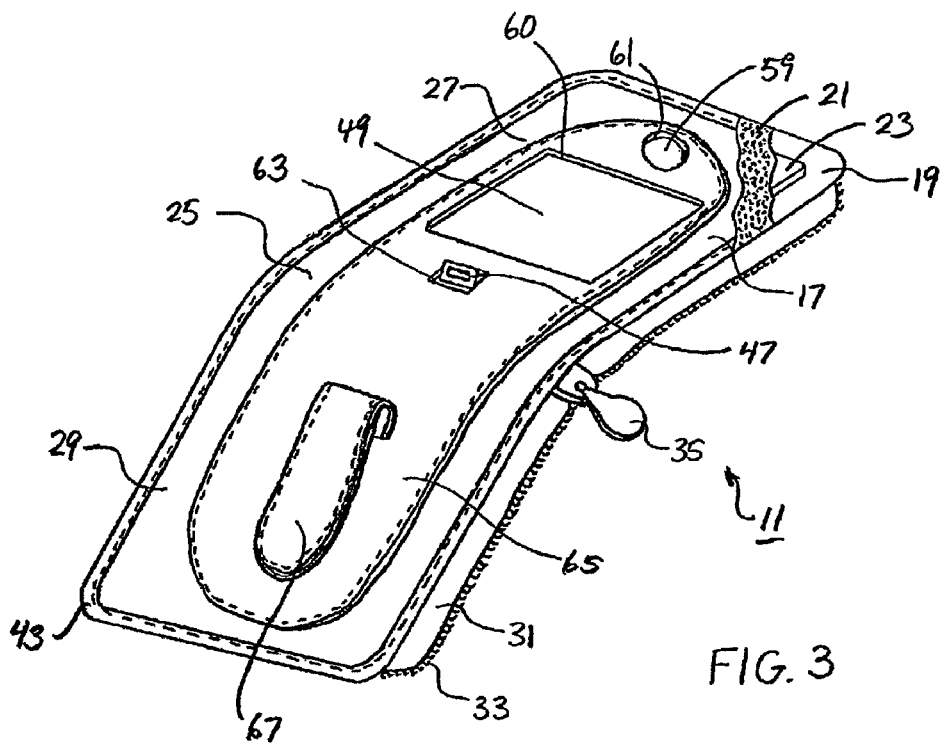
FIG. 3 is a rear perspective view of the blood glucose monitoring kit shown in FIG. 1, the kit being shown with its case opened.
FIG. 4 is a front perspective view of the blood glucose monitoring electronics shown in FIG. 1.

Referring now to FIGS. 1-3, there is shown a blood glucose monitoring kit which is constructed according to the teachings of the present invention and identified generally by reference numeral 11.

Blood glucose monitoring kit 11 comprises a case 13 and blood glucose monitoring electronics 15 which are integrated directly into case 13. As will be described further below, the integration of blood glucose monitoring electronics 15 directly into case 13 serves two principal advantages: (1) to simplify the use of kit 11 in performing a blood glucose assay and (2) to reduce the overall size (i.e., bulkiness) of kit 11.

Case 13 is preferably constructed in the form of a soft-sided, bi-fold wallet which can be disposed between a closed position (as shown in FIG. 1) and an open position (as shown in FIGS. 2 and 3). As will be described further in detail below, case 13 is specifically designed to compactly and comfortably retain all of the individual components which are required to undertake a blood glucose test.

Case 13 includes an outer layer 17 and an inner layer 19 which are secured together (e.g., through a sew line) about their peripheries. Additional layers are preferably disposed between outer and inner layers 17 and 19, as will be described further in detail below.

Outer layer 17 is preferably constructed out of a soft, durable, water resistant, comfortable and aesthetically pleasing material (e.g., a polyester microfiber fabric, leather, rubber, nylon, etc.). Because outer layer 17 is manufactured out of a soft material (i.e., out of a non-rigid material such as plastic), case 13 is considerably comfortable to handle and wear within a traditional clothing pocket, which is a principal object of the present invention.

Inner layer 19 is preferably constructed out of a soft, durable and liquid resistant (i.e., non-porous) material such as nylon or rubber. As will be described further below, the various individual removable components for kit 11 are preferably retained against inner layer 19. Because inner layer 19 is preferably constructed of a liquid resistant material, any liquids (e.g., blood, water, sterilization solutions, etc.) which are present on said components can be easily wiped off layer 17 as needed.

A layer of cushioned material 21 (e.g., cotton, foam, etc.) is preferably disposed between outer layer 15 and inner layer 17. As can be appreciated, layer of cushioned material 21 serves to significantly soften the feel of case 13, thereby rendering it more comfortable to handle and wear, which is a principal object of the present invention.

It should be noted that layer of cushioned material 21 is represented herein as being in the form of a separate layer of material which is disposed between outer layer 15 and inner layer 17. However, it is to be understood that if either outer layer 15 or inner layer 17 is constructed out of an inherently cushioned material, layer cushioned material 21 could be eliminated from case 13 without departing from the spirit of the present invention.

In addition, a pair of spaced apart pair stiffening members 23 are disposed between layer of cushioned material 21 and inner layer 19. Each stiffening member 23 is preferably in the form of a rectangular card which is constructed out of a cardboard material. As can be appreciated, stiffening members 23 serve to provide case 13 with the minimum level of rigidity that is required in order for case 13 to (1) maintain its shape and (2) adequately protect the individual blood glucose components retained therein.

It should be noted that the pair of stiffening members 23 are spaced apart so as to define a narrow area of weakness therebetween, said narrow area of weakness extending laterally across the approximate mid-point of the length of case. This narrow area of weakness created between the pair of stiffening members 23 serves as a fold 25 through which case 13 may bend or flex (i.e., to create the bi-fold design for case 13). Accordingly, fold 25 in case 13 serves to create an upper flap 27 and a lower flap 29 which can be either secured together (to dispose case 13 in its closed position) or spaced apart from one another (to dispose case 13 in its open position).

As will be described further below, inner layer 19 is provided with means for securing the individual removable test components for kit 11 thereagainst. Furthermore, by folding case 13 through fold 25 (i.e., such that upper flap 27 is drawn toward lower flap 29 as shown in FIG. 1), case 13 is closed with all the individual removable components effectively trapped therein. In this manner, the individual removable components are safely retained within case 13 until their use is required, which is highly desirable Means for retaining case 13 in its closed position is preferably provided. Specifically, a narrow band of material 31 is preferably affixed (e.g., sewn) onto inner layer 19 along its outer periphery, material 31 extending orthogonally out from inner layer 19. Furthermore, a zipper 33 is secured onto the free end of band of material 31 and can be operated using a circular paddle 35.

It should be noted that kit 11 is not limited to the use of zipper 33 to retain case 13 in its closed position. Rather, it is to be understood that other means for retaining case 13 in its closed position (e.g., snaps, ties, hook and pile type fasteners, etc.) could be utilized without departing from the spirit of the present invention.

As noted briefly above, means for retaining various removable glucose test components onto inner layer 19 of case 13 is preferably provided. Specifically, as seen most clearly in FIG. 2, a rectangular pouch 37 is affixed (e.g., sewn) to inner layer 19 of lower flap 29 along three of its edges. The one edge of pouch 37 which is not affixed to inner layer 19 is provided with an elastic band 39 which, in the absence of an outside force, constricts tightly against inner layer 19. Pouch 37 is preferably constructed out of a mesh material and serves as a means for retaining small individual components (e.g., individual disposable test strips and individual disposable lancets) against inner layer 19. Access to the components contained within pouch 37 is provided by drawing elastic band 39 substantially away from inner layer 19.

In addition, an elastic band 41 is affixed (e.g., sewn) at both of its ends to inner layer 19 of upper flap 27 in a loop-type configuration. Elastic band 41 is preferably sized and shaped to hold the reusable base of a conventional lancing device (with the individual disposable lancets being retained within pouch 37, as noted above).

Preferably, a reinforcement strip 43 is secured (e.g., sewn) over the outer periphery of both outer layer 17 and inner layer 19. Reinforcement strip 43 is preferably constructed out of a strong and durable material, such as rubber, and serves to reinforce and protect the integrity of the seam joining outer layer 17 to inner layer 19.

As noted briefly above, blood glucose monitoring electronics 15 are permanently integrated directly into case 13. It should be noted that electronics 15 are integrated directly into case 13 without the traditional external plastic housing which protects conventional blood glucose monitors. As can be appreciated, integrating electronics 15 permanently into case 13 without any external plastic housing serves two distinct advantages.

First, the integration of electronics 15 into case without any external plastic housing serves to simplify the use of kit 11 in performing a blood glucose assay. Specifically, because electronics 15 are permanently secured into case 13, the user is not required to withdraw a blood glucose monitor from case 13 before performing each assay. Rather, kit 11 enables a user to perform a glucose calculation with case 13 in either its open or closed positions, as will be described further below.

Second, the integration of electronics 15 into case without any external plastic housing serves to significantly reduce the overall size (i.e., bulkiness) of kit 11 when case 13 is closed. As a result, a user can more comfortably wear and/or hold kit 11 on his/her person between tests, which is a principal object of the present invention.

For purposes of simplicity, electronics 15 are described herein as being designed principally for use in the measurement of the concentration of glucose in a blood sample. However, it is to be understood that electronics 15 are not limited to the measurement of glucose in a blood sample. Rather, kit 11 could integrate the electronics for alternative types of analyte test instruments (e.g., keytone test instruments) into case 13 without departing from the spirit of the present invention.

Electronics 15 (shown in isolation in FIG. 4) preferably includes a double sided printed circuit board (PCB) 45 on which various electrical components are mounted, as will be described below. It should be noted that printed circuit board 45 serves to electrically connect the various electrical components mounted thereon.

A multi-purpose test port 47 is mounted on printed circuit board 45 along one of its edges. Test port 47 is a current source sensing device which is capable of transmitting and receiving serial data. In the present embodiment, test port 47 includes a slot shaped to matingly receive and electrically connect with, inter alia, a test strip, a calibration strip, or the interface connector of a hardwire communication link.

A display 49 is mounted on printed circuit board 45 and is electrically connected thereto by means of a ribbon cable 51. Display 49 is preferably in the form of a liquid crystal display (LCD) which can be used to display, inter alia, test results, user messages, and recalled information which is stored in the memory of electronics 15.

A battery compartment 53 is mounted on printed circuit board 45 in electrical connection thereto. Compartment 53 is sized and shaped to receive a pair of replaceable AA-type batteries 55 which, in turn, serve as the power source for driving the operation of electronics 15. It should be noted that electronics 15 need not derive its power from two AA-type batteries 55. Rather, it is to be understood that electronics 15 could derive power from alternative power sources (e.g., a single coin cell battery) without departing from the spirit of the present invention.

Additional components which are preferably mounted onto printed circuit board 45 include, inter alia, a microprocessor (not shown) for performing the principal calculation and data management tasks for electronics 15 and memory (not shown) for retaining data processed by the microprocessor.

In addition, printed circuit board 45 includes a switch 57 for controlling the operative functions of electronics 15. A circular button 59 is provided for regulating switch 57. Specifically, the manual depression of button 59 serves to close switch 57 which, in turn, enables the user to, among other things, regulate the power state of electronics 15, recall information stored in memory, respond to messages provided in the display and set some of the configuration control parameters.

Electronics 15 are disposed directly into upper flap 27 between outer layer 17 and inner layer 19. Preferably, a rectangular window 59 is formed in upper flap 27 so as to render display 49 externally visible. Optionally, a transparent piece of plastic (not shown) may be mounted over window 59 to protect the screen for display 49. In addition, it should be noted that electronics 15 are disposed within upper flap 27 such that battery compartment 53 protrudes through inner layer 19 (as seen most clearly in FIG. 2). In this manner, batteries 55 are accessible to the user for replacement when deemed necessary.

Similarly, a circular opening 61 is provided in upper flap 27 so as to render button 59 externally accessible. Furthermore, a square-shaped opening 63 is provided in upper flap 27 so as to render test port 47 externally accessible. In this manner, the insertion of a test strip into test port 47, the manual depression of button 59 in order to commence an assay and the visual display of test results on display 49 can all be achieved with case 13 configured in either its open or closed positions, thereby simplifying the use of kit 11, which is highly desirable.

It should be noted that case 13 may additionally include an elongated protective patch 65 which is secured (e.g., sewn) onto the surface of outer layer 17. Patch 65 is preferably constructed out of a strong and durable material, such as rubber, and serves to facilitate the handling of case 13. Also, a belt loop 67 constructed out of a similar material as patch 65 is preferably secured at one end onto patch 65 along the lower flap 29. The free end of belt loop 67 preferably releasably secures onto patch 65 (e.g., using hook and pile type fasteners) in order to create a closed loop, thereby enabling kit 11 to be worn on the belt of a patient.

Although not shown herein, it should be noted that case 13 could be constructed to include a protective cover. Specifically, upper flap 27 could be provided with a pivotable strip of material which can be selectively positioned over display 49, button 59 and test port 47 when electronics 15 is not in use. Disposed as such, the strip of material would serve as both a protective cover for shielding sensitive components of electronics 15 from potentially harmful environmental elements (e.g., moisture) and a shield for disguising the relatively conspicuous (and potentially embarrassing) nature of display 49, button 59 and test port 47.

It should also be noted that kit 11 is not limited to display 49 being externally visible. Rather, it is to be understood that electronics 15 could be integrated into upper flap 27 such that display 49 is visible through a window formed in inner layer 19 rather than outer layer 17 (i.e., with display 49 visible from inside case 13 rather than outside case 13). Similarly, button 59 and test port 47 could be alternatively configured for access through inner layer 19 of upper flap 27. In this manner, with case 13 disposed in its closed position, display 49, button 59 and test port 47 would all be hidden from view and protected from potentially harmful environmental elements.

In use, kit 11 can be used in the following manner to monitor blood glucose levels. Specifically, kit 11 is preferably stored with case 13 configured in its closed position. As noted above, the compact nature and soft cushioned feel of case 13 renders kit 11 very easy to store and/or wear. When a blood glucose test is required, case 13 is opened by unzipping zipper 33 and pivoting upper flap 27 away from lower flap 29.

With case 13 opened, the user can withdraw the reusable lancing device base (not shown) from elastic band 41 as well as a disposable lancet (not shown) from pouch 37. The disposable lancet is then unwrapped and installed into the lancing device base, thereby rendering the lancing device ready for a subsequent skin prick.

Similarly, a disposable test strip (not shown) is removed from pouch 37 and unwrapped from any protective packaging. The unwrapped test strip is then inserted into the slot of test port 47 which, in turn, automatically activates (i.e., turns "on") the glucose monitor. Furthermore, upon detecting the presence of the test strip within port 47, the activated monitor generates a "ready" indication on display 49.

Having completed the aforementioned preparatory steps, the user then uses the lancet device to acquire a blood sample. In turn, blood exiting from the patient's wound site is deposited onto the reactive area of the test strip. The blood sample then reacts with enzymes in the reactive area which, in turn, produces an electrical response in the form of a decaying electrical current. The decaying current is then converted by electronics 15 into a digital signal that is processed by the microprocessor to determine the analyte test value that corresponds to the signal. The microprocessor then stores the analyte test data in memory and simultaneously registers the analyte test value on display 49 for the patient to read.

Upon completion of the test, the used lancet and test strip are disposed and the lancet device base is returned to its stored position within elastic band 41. The user can then zip case 13 back to its closed position for storage until such time that future glucose testing is desired.

The embodiment shown in the present invention is intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A blood glucose monitoring kit, comprising:
   a foldable case comprising:
      a first flap;
      a second flap; and
      a fold between the first flap and the second flap, wherein the foldable case folds and unfolds about the fold; and
   blood glucose monitoring electronics integrated within the foldable case, wherein the blood glucose monitoring electronics comprise:
      a test port that is externally accessible from outside of the foldable case when folded, wherein the test port is externally accessible through an opening in the fold in the case; and
      a display to display test results that is externally visible from the outside of the foldable case when folded;
   wherein the blood glucose monitoring electronics are operational to perform a blood glucose test when the case is folded.

2. The blood glucose monitoring kit of claim 1, wherein the foldable case comprises:
   an inner layer;
   an outer layer; and
   a layer of cushioned material disposed between the outer layer and the inner layer.

3. The blood glucose monitoring kit of claim 2, wherein the inner and outer layers are constructed out of a non-plastic material.

4. The blood glucose monitoring kit of claim 2, wherein the inner and outer layers are constructed out of a soft fabric material.

5. The blood glucose monitoring kit of claim 2, wherein the case comprises a pair of stiffening members that are disposed between the inner layer and outer layer, and wherein the pair of stiffening members are spaced apart so as to define the fold in the case about which the case bends.

6. The blood glucose monitoring kit of claim 5, wherein the test port is externally accessible through an opening in the outer layer.

7. The blood glucose monitoring kit of claim 1, comprising means for securing the case in the closed position.

8. The blood glucose monitoring kit of claim 1, comprising a zipper coupled to the outer periphery of the foldable case for retaining the case folded.

9. The blood glucose monitoring kit of claim 1, wherein the blood glucose monitoring electronics include a switch formed on a printed circuit board, wherein the switch is triggered by a button that is externally accessible from the outside of the foldable case when folded.

10. The blood glucose monitoring kit of claim 1, comprising a pouch secured onto the foldable case, the pouch on an inside of the foldable case when folded.

11. The blood glucose monitoring kit of claim 10, comprising a lancing device holding means.

12. The blood glucose monitoring kit of claim 1, wherein the pouch comprises an elastic band that constricts tightly against the inside of the foldable case so as to enable the pouch to fold and unfold.

13. The blood glucose monitoring kit of claim 1, comprising a zipper coupled to the outer periphery of the foldable case for retaining the case folded.

14. The blood glucose monitoring kit of claim 1, comprising a battery compartment mounted on a printed circuit board and disposed on an inside of the foldable case.

\* \* \* \* \*